(12) United States Patent
Stecklein et al.

(10) Patent No.: US 7,718,433 B2
(45) Date of Patent: May 18, 2010

(54) PACKAGING SYSTEM FOR A STERILIZED ARTICLE

(75) Inventors: Gregory Stecklein, Lake Villa, IL (US); Michael Duski, Wheeling, IL (US); Andrew G. Rozycki, Columbus, OH (US)

(73) Assignee: Allegiance Corporation, McGaw Park, IL (US)

( * ) Notice: Subject to any disclaimer, the term of this patent is extended or adjusted under 35 U.S.C. 154(b) by 1098 days.

(21) Appl. No.: 10/970,451

(22) Filed: Oct. 21, 2004

(65) Prior Publication Data

US 2006/0088450 A1 Apr. 27, 2006

(51) Int. Cl.
*B01L 9/00* (2006.01)
(52) U.S. Cl. .................. 436/10; 422/102; 422/119; 422/99; 422/50; 436/8
(58) Field of Classification Search ............. 436/10, 436/8; 422/28, 102, 99, 50, 119; 53/469; 206/439; 383/88
See application file for complete search history.

(56) References Cited

U.S. PATENT DOCUMENTS

| | | | |
|---|---|---|---|
| 5,222,600 A | 6/1993 | Stoddard et al. | 206/370 |
| 5,459,978 A | 10/1995 | Weiss et al. | 53/425 |
| 5,590,777 A | 1/1997 | Weiss et al. | 206/439 |
| 5,620,656 A * | 4/1997 | Wensky et al. | 422/28 |
| 5,635,134 A | 6/1997 | Bourne et al. | 422/26 |
| 5,638,661 A | 6/1997 | Banks | 53/469 |
| 5,653,090 A | 8/1997 | Weiss et al. | 53/425 |
| 5,879,620 A | 3/1999 | Cohen | 422/1 |
| 5,958,337 A | 9/1999 | Bourne et al. | 422/26 |
| 6,159,423 A | 12/2000 | Bourne et al. | 422/26 |
| 6,406,674 B1 | 6/2002 | Bourne et al. | 422/292 |
| 6,406,764 B2 | 6/2002 | Bayer | 428/35.2 |
| 6,517,916 B1 | 2/2003 | Bayer et al. | 428/34.3 |
| 6,578,348 B1 | 6/2003 | Banks | 53/425 |
| 6,630,104 B1 | 10/2003 | Bayer | 422/1 |
| 6,672,036 B2 | 1/2004 | Banks | 53/459 |
| 6,715,263 B2 | 4/2004 | Banks | 53/425 |

(Continued)

FOREIGN PATENT DOCUMENTS

WO   WO 01 10473   *   2/2001

*Primary Examiner*—Walter D Griffin
*Assistant Examiner*—Christine T Mui
(74) *Attorney, Agent, or Firm*—Arent Fox LLP

(57) ABSTRACT

A packaging system in accordance with the principles of the present invention includes a sterilization pouch. The pouch includes a posterior portion attached to an anterior portion along three edges. The two portions define the pouch. The top part of the pouch is inverted so that the inside part of the pouch is facing outward and forms a cuff around the pouch. An integral internal sterilization indicator is further provided. The integral indicator comprises a sterilizing agent sensitive substance. The sterilizing agent sensitive substance can be an indicator ink printed as an ink line on the interior of the sterilization pouch below the cuff. Thus, the indicator becomes visible during aseptic delivery of the packaged article to provide a clear indication as to whether or not adequate conditions for sterilization have been achieved. In a further embodiment, the indicator ink line repeats as a pattern throughout the interior of the sterilization pouch. Alternatively, the indicator could be printed as an ink line on the exterior of the sterilization pouch below the cuff. In a further embodiment, both interior and exterior printing could be used.

55 Claims, 5 Drawing Sheets

U.S. PATENT DOCUMENTS

| | | | |
|---|---|---|---|
| 2002/0092274 A1 | 7/2002 | Banks | 53/459 |
| 2003/0123759 A1 | 7/2003 | Banks | 383/88 |
| 2005/0092636 A1* | 5/2005 | Su-Syin | 206/363 |

* cited by examiner

PACKAGING SYSTEM FOR A STERILIZED ARTICLE

FIELD OF THE INVENTION

The present invention relates to a packaging system for packaging a sterilizable article for aseptic presentation onto a sterile field.

BACKGROUND OF THE INVENTION

Since the mid-nineteenth century, medical professionals have recognized the need for maintaining sterile conditions, especially in operating rooms. Joseph Lister, *"On the Antiseptic Principle of the Practice of surgery"* (1867); Vol. XVIII, Part 6. The Harvard Classics. New York: P.F. Collier & Son, 1909-14.Thus, equipment covers, patient drapes, and other medical supplies often are used only a single time. In addition, ready-to-use articles are frequently purchased from commercial manufacturers. Alternatively, the articles, whether reusable or single-use, may be processed within a facility providing health care such as a hospital, surgical center, clinic or office. The processor must package the article in a manner that will protect and maintain both the sterility of the article and the sterility of the surgical field during the introduction of the article.

Various sterilization treatments exist, such as, for example, steam, ethylene oxide, radiation, formaldehyde, hydrogen peroxide, peracetic acid, glutaraldehyde, ozone, and dry-heating. Traditionally, many articles intended for use in a surgical field are double packaged in a completely sealed outer packaging element that surrounds an inner packaging element in or on which the sterilizable article is located. The double-packaged article is sterilized so that when the article arrives at the point of use, both the article and the inner packaging element are sterile.

It is particularly important that sterile technique be practiced during unwrapping or during opening of a package. For example, sterile technique does not allow a hand or object to contact a sterile article. To introduce a double-packaged sterile article onto a sterile field, typically a non-scrubbed attendant opens and discards the outer packaging element surrounding the inner packaging element and the article. The attendant then carefully opens the inner packaging element and presents the sterile article to scrubbed personnel for transfer to the sterile field. The non-scrubbed attendant must exercise great care in order to maintain the sterility and integrity of the article and thus the sterile field.

The inner packaging element is intended to provide a second level of protection and to maintain the sterility of the article and of the sterile field during introduction of the article. An example of a typical inner packaging element employs a double-layered muslin cloth, commonly known as a central supply wrap (CSR), a name that originally identified the hospital central supply department as the source of the packaged article. In a CSR wrap, an article is placed on a diagonal in the center of a square sheet of fabric that is proportionally sized to adequately enclose the article. Each corner of the sheet is folded over the article sequentially, and the fourth corner is tucked under the first three proximate the center of the article. The end of the fourth corner is left exposed for later opening of the package.

When opening a CSR wrap, the non-scrubbed attendant holds the package in one hand and with the other hand grasps the exposed corner at the tab, pulls the corner of the sheet away from the attendant around and under the holding hand, and tucks the corner into the holding hand. The attendant pulls each corner of the sheet away from the article and around the holding hand, tucking the corners between the fingers of the holding hand to provide a protective hand cover. Since only the holding hand has a protective cover when the article has been exposed, the non-scrubbed attendant preferably is assisted by a second, scrubbed person who removes the sterile article from the holding hand and who actually introduces the sterile article onto the sterile field.

When the non-sterile attendant is opening the CSR wrap, if any edge of the sheet escapes the holding hand or inadvertently touches the sterile article, the article has been contaminated. Discarding the contaminated article increases the cost of the procedure, both in terms of actual articles used and total time expended during the procedure. In addition, CSR wrap is prone to fluid strike-though and exhibits tearing with extended use. Further, sterilization methods employing cloth wrap are normally practiced by first unwrapping the sterilized tray, followed by moving the unwrapped tray to an area where the tray contents will be used. Because sterile technique requires careful and precise procedures, cloth wrap practice is time consuming and expensive.

An alternative practice replaces muslin wrap with a disposable non-woven CSR wrap applied in the same manner. Although non-woven CSR wraps offer improved fluid resistance and improved bacterial barrier migration over cloth counterparts, sterilization practices that use these nonwoven materials are still labor intensive and costly.

In addition, attempts exist in the prior art to address the need for a packaging system that permits opening of the system without significant risk of contamination or damage to the article combined with easy aseptic presentation of the article for use. In one prior art approach, a packaging system includes a sterilizable, flexible, elongate-tubular member having an outside, a closed end and an open end. A sterilizable article is placed into the sterilizable tubular member so that the article contacts a portion of an inside surface at the closed end of the tubular member. A border portion with a first edge and a second edge is formed on the tubular member. The first edge of the border portion is attached to the tubular member proximate an opening in the tubular member for the opening. The second opposing edge of the border portion is spaced apart from the first edge by a width of the border portion. A fold line is formed in the border portion and the tubular member above the article. The article is enclosed in the tubular member by placing the first edge of the border portion under the second edge of the border portion between the border portion and the tubular member. After sterilization, the article can be dispensed from the sterile tubular member and transferred onto a sterile field by a single non-scrubbed attendant while maintaining the sterility and integrity of the article and the field.

While these type of packaging systems improve the time and costs of presenting sterilized articles, the danger of contamination is still nevertheless real and present. If such a contaminated article is introduced onto the sterile field, the entire field will be contaminated and the potential for postoperative infection increased, which increases both the cost and the risk of the medical procedure.

In attempting to address this risk, the Association for the Advancement of Medical Instrumentation ("AAMI"), 1110 North Glebe Road, Suite 220, Arlington, Va. 22201-4795 and the Association of periOperative Registered Nurses ("AORN"), 2170 South Parker Rd, Suite 300, Denver, Colo. 80231-5711 standards state that an internal chemical indicator should be used within each package to be sterilized. The internal indicator may be a single-parameter indicator (Class 3), mulit-parameter indicator (Class 4) or integrating indicator (Class 5), depending on the complexity of the pack and contents. Thus, an independent indicator strip is typically placed into prior art packaging. However, when an article is aseptically presented as described above, the strip often falls to the floor, is not be easily seen, and can lead to non-optimal aseptic delivery.

What is thus needed is a packaging system that minimizes the time and costs of presenting sterilized articles. Such article should decrease the instances in which the attendant is unaware of a contamination, thereby decreasing the potential for post-operative infection.

SUMMARY OF THE INVENTION

A packaging system in accordance with the principles of the present invention minimizes the time and costs of presenting sterilized articles. A packaging system in accordance with the principles of the present invention decreases the instances in which the attendant is unaware of a contamination, thereby decreasing the potential for post-operative infection. A packaging system in accordance with the principles of the present invention eliminates the need for an independent indicator strip placed into the packaging while effectively indicating a contaminated state.

A packaging system in accordance with the principles of the present invention includes a sterilization pouch. The sterilization pouch comprising a sterilizable, flexible, elongate-tubular member having an outside, a closed end and an open end. The top part of the pouch is inverted so that the inside part of the pouch is facing outward and forms a cuff around the pouch. An integral internal sterilization indicator is provided. The integral indicator comprises a sterilizing agent sensitive substance. The sterilizing agent sensitive substance can be an indicator ink printed as an ink line on the interior of the sterilization pouch below the cuff. Thus, the indicator becomes visible during aseptic delivery of the packaged article to provide a clear indication as to whether or not adequate conditions for sterilization have been achieved. In a further embodiment, the indicator ink line repeats as a pattern throughout the interior of the sterilization pouch. Alternatively, the indicator could be printed as an ink line on the exterior of the sterilization pouch below the cuff. In a further embodiment, both interior and exterior printing could be used.

DETAILED DESCRIPTION OF AN EXEMPLARY EMBODIMENT

Figure 1:
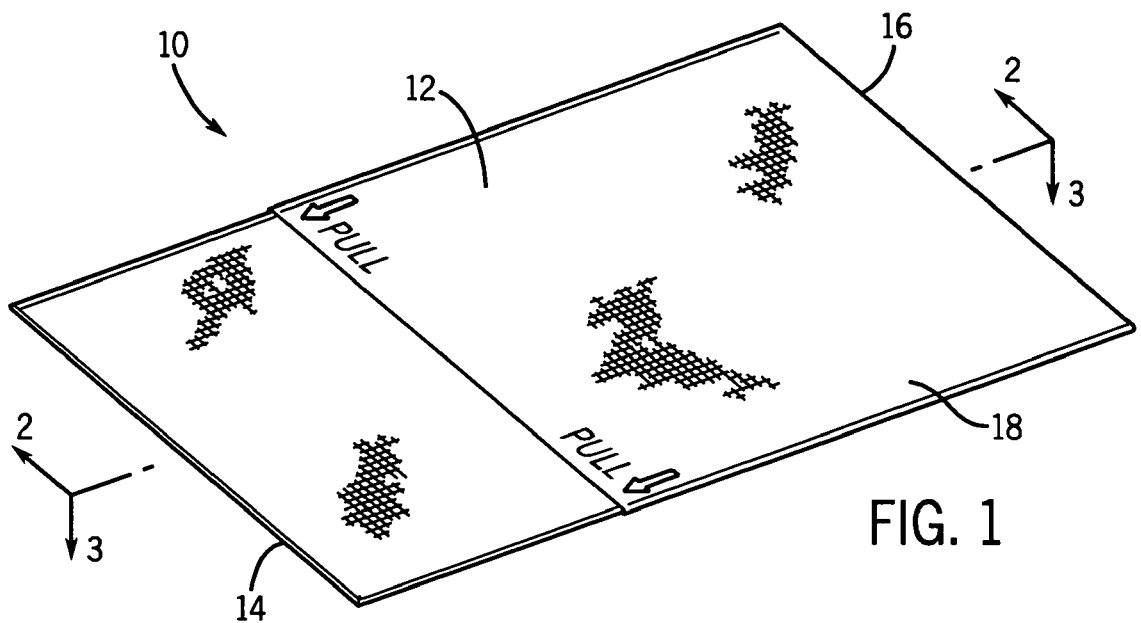
FIG. 1 is a perspective view of an exemplary packaging system for a sterilizable article in accordance with the principles of the present invention.

Referring to FIGS. 1-5, an exemplary packaging system for a sterilizable article in accordance with the principles of the present invention is seen. The packaging system includes a sterilization pouch 10. The sterilization pouch 10 comprising a sterilizable, flexible, elongate-tubular member having an outside 12, an inside 13, a closed end 14 and an open end 16. In one embodiment, the elongate-tubular member can comprise a posterior portion attached to an anterior portion along three edges, with the two portions defining the sterilization pouch 10. In one embodiment, the elongate-tubular member can comprise a posterior portion attached to an anterior portion along three edges, with the two portions defining the sterilization pouch 10. In another embodiment, the elongate-tubular member can comprise a folded single sheet seamed on two sides. The top part of the sterilization pouch 10 can be inverted so that the inside part of the pouch is facing outward and forms a cuff 18 around the sterilization pouch 10.

Figures 4, 5:
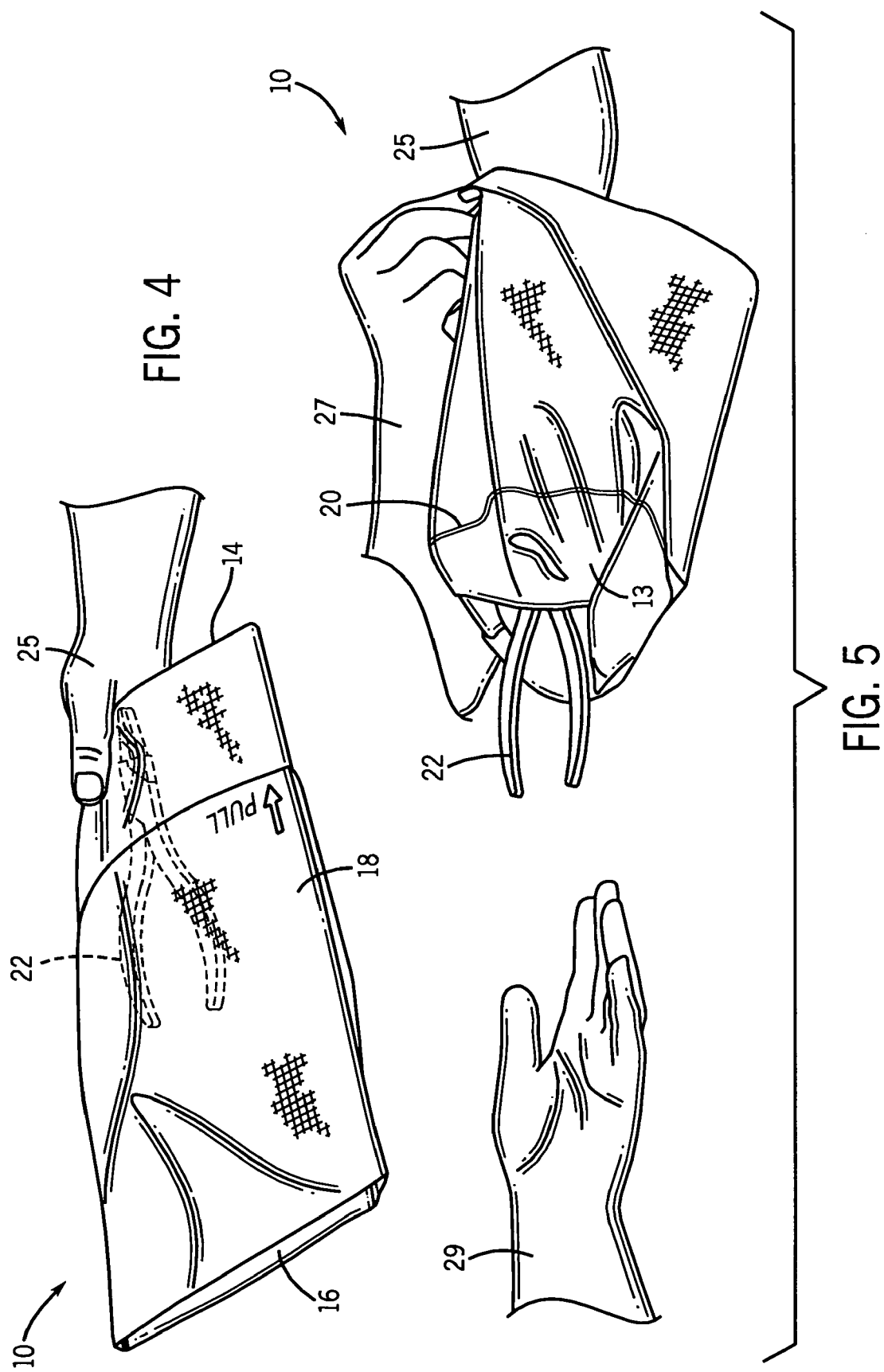
FIG. 4 is view showing an article being prepared for presentation from the exemplary packaging system for a sterilizable article of FIG. 1.
FIG. 5 is view showing an article being presented from the exemplary packaging system for a sterilizable article of FIG. 1

Thus, the sterilization pouch 10 is adapted to be aseptically presented by inverting the sterilization pouch 10. FIG. 4 shows an article 22 being prepared for presentation from the exemplary packaging system. The user grasps the article 22 through the closed end 14 of the sterilization pouch 10 with a first hand 25. The user 25 then pulls-back the open end 16 of the sterilization pouch 10 with their second hand 27, by grasping in the FIGS. 1-5 embodiment the cuff 18, thereby exposing the article 22 for the health care professional 29 in the sterile environment. This is seen in FIG. 5.

A sterilization pouch 10 in accordance with the principles of the present invention encompasses a broad range of possible fibrous or non-fibrous materials. For example, a sterilization pouch in accordance with the present invention can comprise a typical nonwoven (fiborous) constructs such as a spunbond/meltblown/spunbond (SMS) or modified constructs. In another embodiment, a sterilization pouch in accordance with the present invention can comprise a nonwoven (fiborous) material that combines a strength layer such as SpunBonded Polypropylene (SBPP) and at least one filtration layer such as meltblown, or other forms of fiborous media. In another embodiment, a sterilization pouch in accordance with the present invention can comprise spunlace, flashspun, wetlaid, drylaid, and carded fiborous nonwoven processes.

For further example, a sterilization pouch in accordance with the present invention can comprise a non-fiborous such as composites that may contain as one layer a microporous or apertured film and possibly a scrim or film netting material. The microporous film can act as a media layer, while a scrim or netting could accentuate strength.

In another embodiment, a film for a sterilization pouch in accordance with the present invention can comprise a bicomponent or bi/trilaminant of polypropylene (PP), polyethylene formulated (PE) or Nylon synthetic polymer available from E. I. du Pont de Nemours and Company, Wilmington, Del., USA. From a materials standpoint, a sterilization pouch in accordance with the present invention can comprise from a polyolefin, such as for example polypropylene, polyethylene or polyester, as well as natural fibers cellulose and cellulose, synthetic fiber blends. In a preferred embodiment, a sterilization pouch in accordance with the present invention is made of a uniform material. Of course, one of ordinary skill would know how to assembly/manufacture sterilization pouch in accordance with the present invention using convention and readily available techniques and equipment.

A packaging system in accordance with the principles of the present invention further includes an integral sterilization indicator 20. In the exemplary embodiment seen in FIGS. 1-5, the integral sterilization indicator 20 is printed on the interior (seen in FIG. 3). As seen in FIG. 5, when the article 22 is presented to the user 29 in the sterile environment, the integral sterilization indicator 20 is exposed to the user 29 such that the user 29 can easily see whether the article 22 was properly sterilized.

The integral indicator comprises a sterilizing agent sensitive substance. As used herein, "agent" means a substance responsive to sterilization environments such as for example temperature or gases exposure and "sterilizing agent sensitive substance" means a substance capable of having a first indicating state prior to being exposed to a predetermined sterilization procedure and a second indicating state after exposure to at least a portion of the sterilization procedure (preferably the entire sterilization procedure). Preferably, the first indicating state of the substance comprises a first color and the second indicating state of the substance comprises a second color that is visually distinguishable from the first color. The first state also can be a substantially clear or transparent or translucent state, and the second state can be a substantially opaque or colored state. The converse of these states could also be employed.

Figures 2, 3:
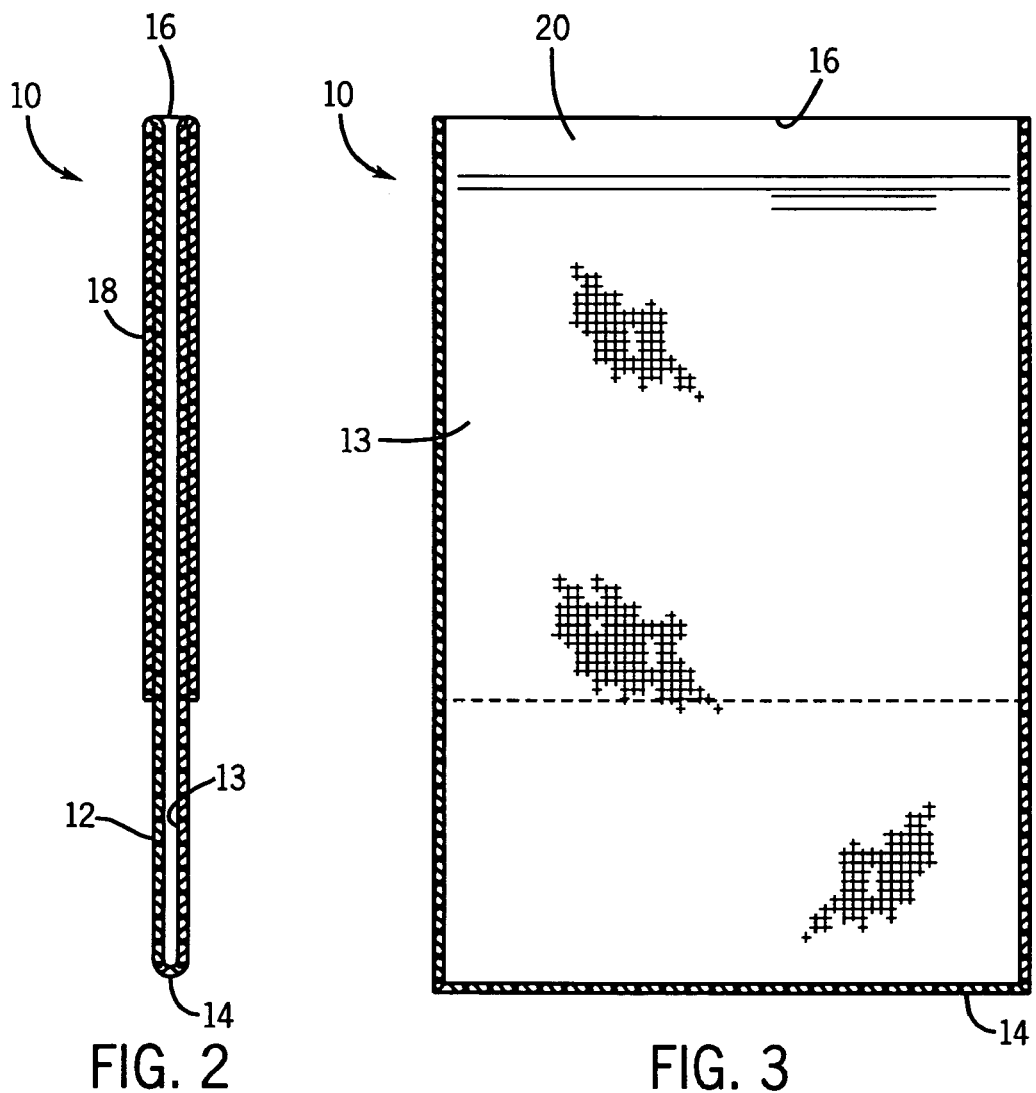
FIG. 2 is a cross-sectional side view of the exemplary packaging system for a sterilizable article of FIG. 1.
FIG. 3 is an interior view of the exemplary packaging system for a sterilizable article of FIG. 1.

As seen in FIG. 3, the sterilizing agent sensitive substance 20 can be located on the interior of the sterilization pouch 10 below the cuff such that the sterilizing agent sensitive substance 20 becomes visible as product begins to be aseptically presented. In a preferred embodiment, below the cuff means that the ink is printed on the interior close to the top of the pouch so that the printed ink will be visually seen as soon as the product begins to be aseptically presented, although use of the term herein is not intended to be specifically narrowed to that precise position. Thus, the indicator becomes visible during aseptic delivery of the packaged article to provide a clear indication as to whether or not adequate conditions for sterilization have been achieved.

In one embodiment of the present invention, the sterilizing agent sensitive substance can be an indicator ink printed as an ink line on the interior of the pouch approximately 1 inch below the cuff. "Printed" as used herein refers to any manner of creating visibly perceptible marking on the surface. Printed is meant to be broadly defined herein and includes alternative methods of affixing a visibly perceptible marking such as for example permanently affixing an indicator strip. An example of such indicator ink is available from Steritec Products Mfg. Co., Inc., 599 Topeka Way, Suite 700, Castle Rock, Colo. 80109.

Figure 6:
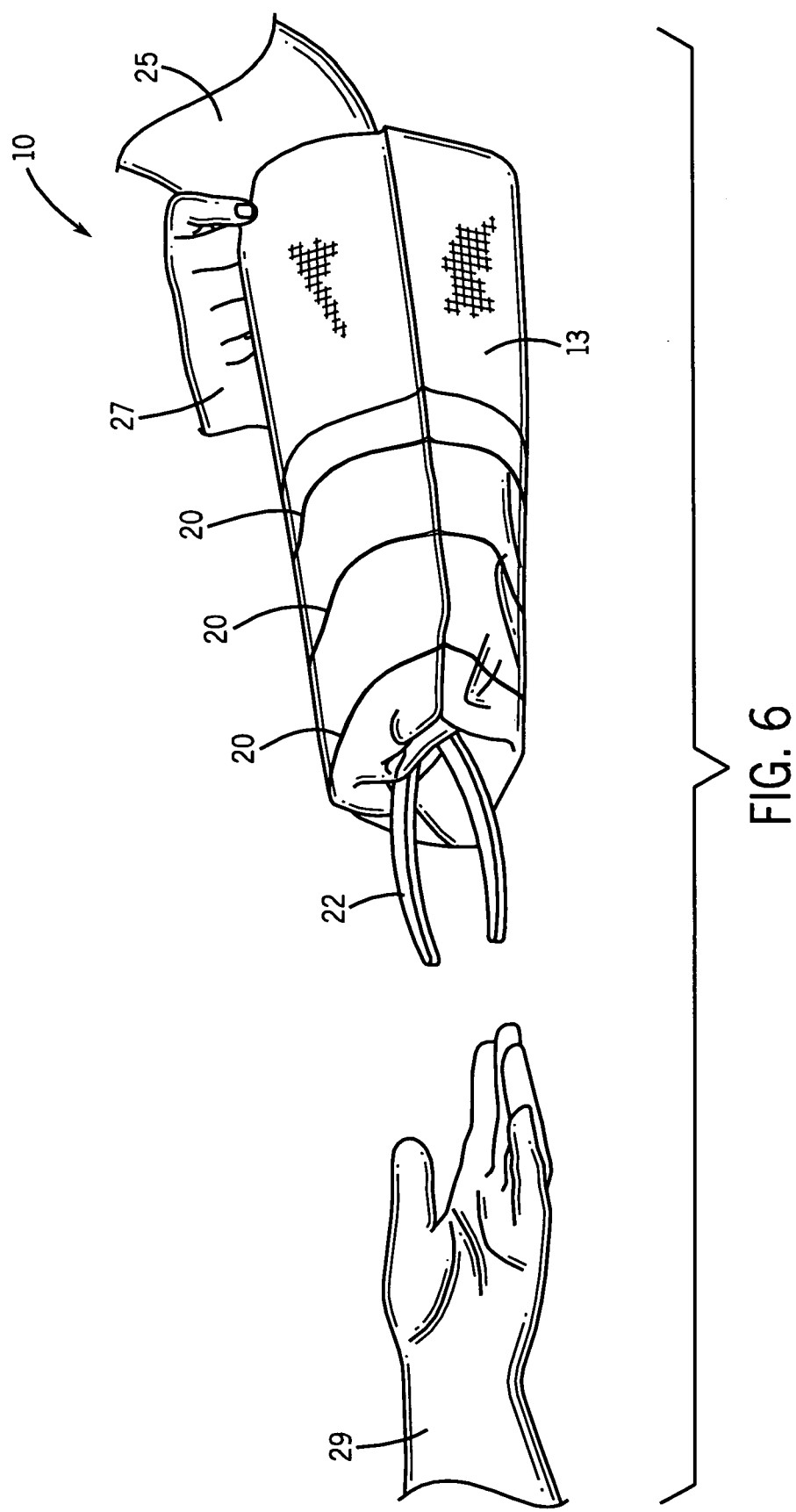
FIG. 6 is view showing an article being presented from an alternative packaging system for a sterilizable article in accordance with the principles of the present invention.
Figure 7:
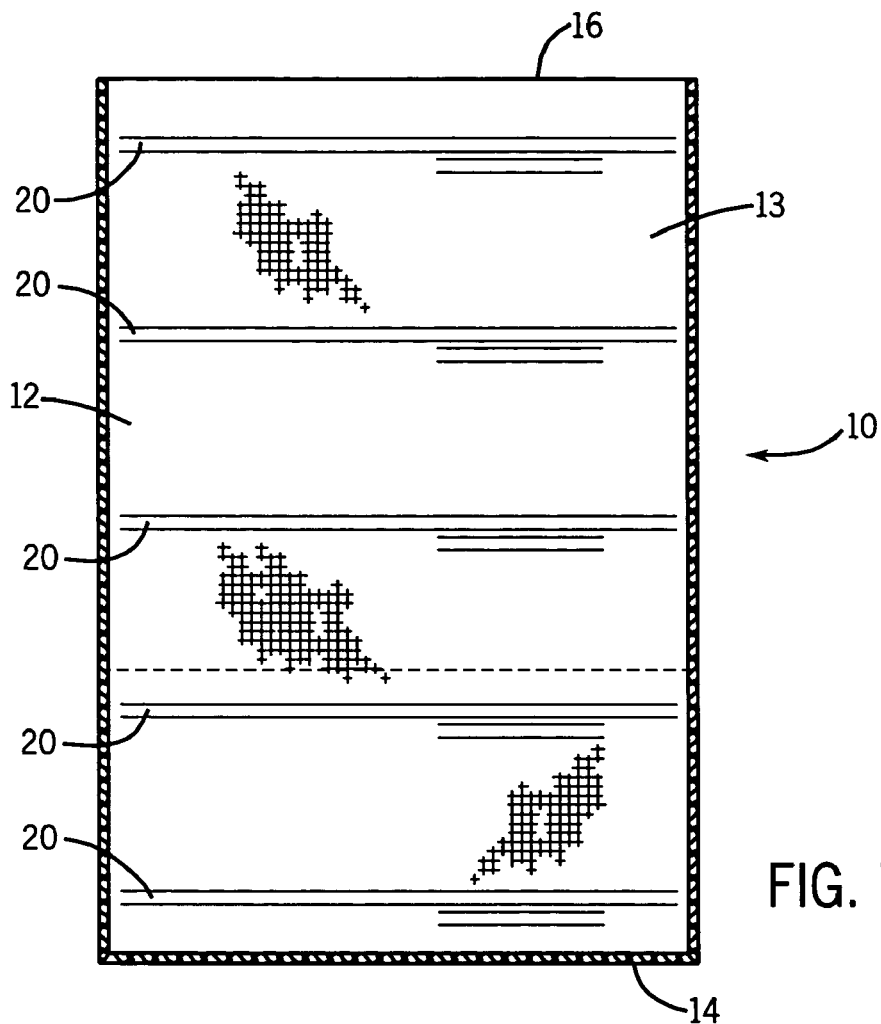
FIG. 7 is an interior view of the alternative packaging system for a sterilizable article of FIG. 6.

In a further embodiment, the sterilizing agent sensitive substance 20 repeats as a pattern in the interior of the sterilization pouch 10. This further embodiment is seen in FIGS. 6 and 7. As with FIG. 5, in FIG. 6 an article 22 is being presented from the packaging system for a sterilizable article 10. When the article 22 is presented to the user 29 in the sterile environment, the multiple integral sterilization indicators 20 are exposed to the user 29 such that the user 29 can easily see whether the article 22 was properly sterilized. FIG. 7 shows an interior view of the alternative packaging system for a sterilizable article of FIG. 6 the multiple integral sterilization indicators 20. In a further embodiment, the sterilizing agent sensitive substance could be on the cuff.

Figure 8:
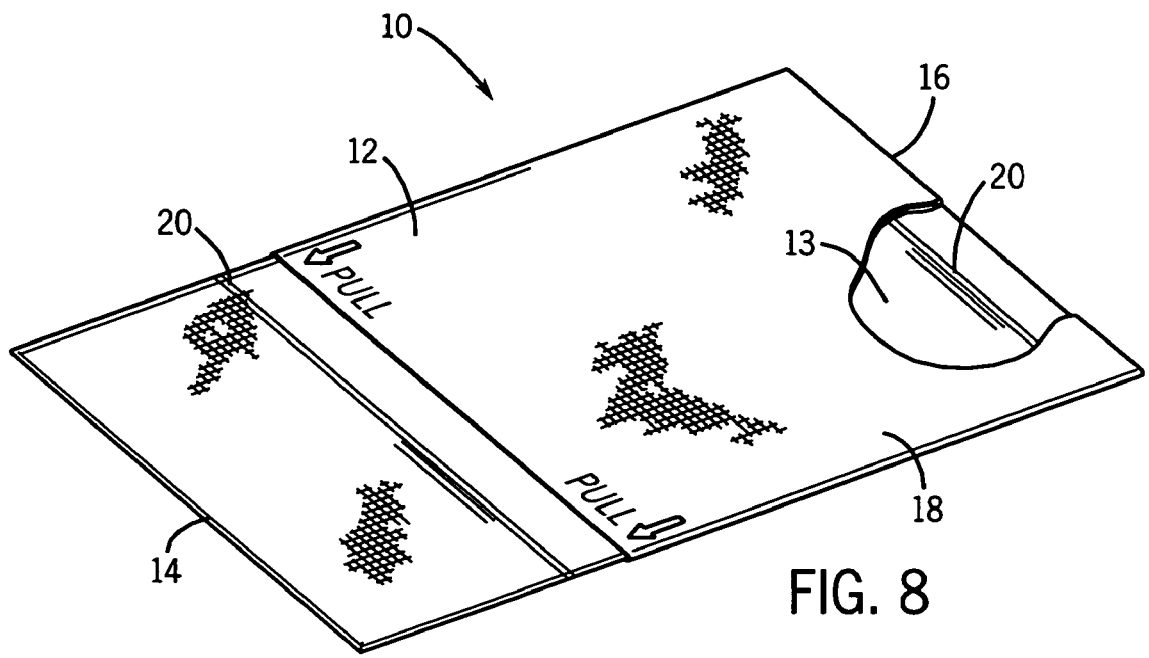
FIG. 8 is a perspective view of another alternative packaging system for a sterilizable article in accordance with the principles of the present invention
Figure 9:
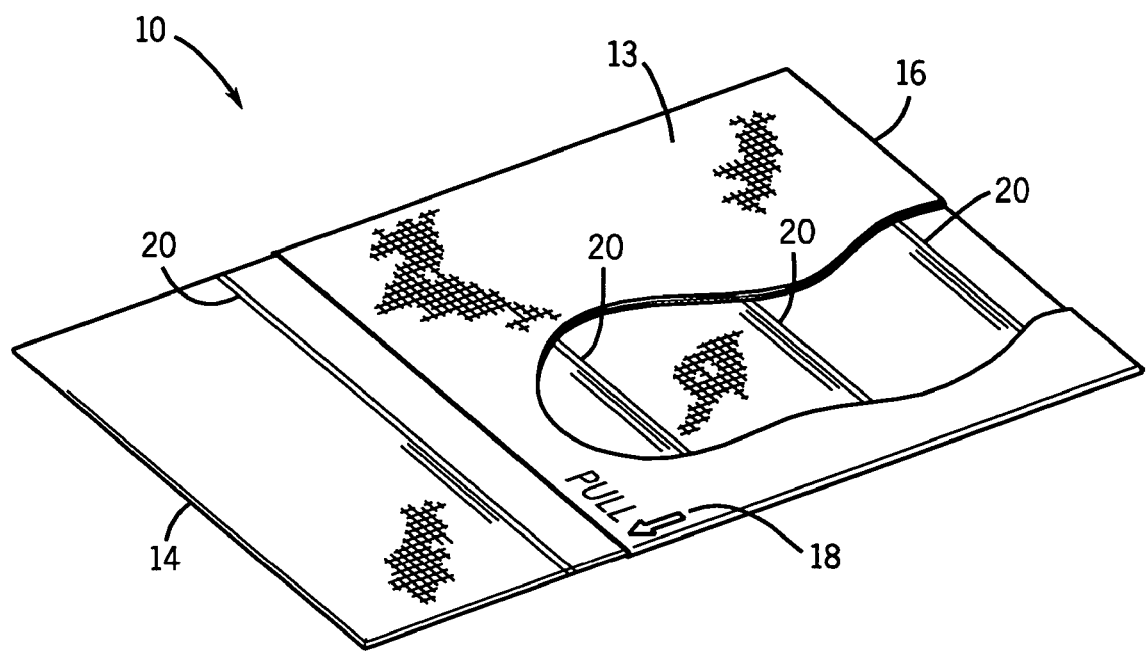
FIG. 9 is a perspective view of yet another alternative packaging system for a sterilizable article in accordance with the principles of the present invention.

In a further embodiment, the sterilizing agent sensitive substance 20 is printed on both the interior and exterior of the sterilization pouch 10. This embodiment is seen in FIG. 8. In a further embodiment, the sterilizing agent sensitive substance 20 repeats as a pattern in the interior of the sterilization pouch 10 on both the interior and exterior of the sterilization pouch 10. This embodiment is seen in FIG. 9. In a further embodiment, the sterilizing agent sensitive substance can be printed only on the exterior of the sterilization pouch.

The sterilizing agent sensitive substance can be sensitive to any one of a wide variety of sterilization processes. For example, the sterilizing agent sensitive substance can be sensitive to those sterilization procedures that utilize different sterilizing agents such as for example hydrogen peroxide, peracetic acid, ozone, steam, dry heat, ethylene oxide, formaldehyde, radiation, and combinations thereof as a sterilant or as an element in a step in the procedure. The sterilizing agent sensitive substance can be practiced with procedures that utilize matter in a variety of states such as liquids, gases, fluids, plasmas, and combinations thereof.

For example, the sterilizing agent sensitive substance can be sensitive to hydrogen peroxide sterilization procedures. As used herein, vapor phase, liquid phase and plasma hydrogen peroxide sterilization procedures are all within the broad definition of hydrogen peroxide sterilization procedures. Sterilization procedures that utilize hydrogen peroxide as merely a component during a substantial portion of the procedure are also included within the meaning of the hydrogen peroxide sterilization procedure.

In a further embodiment of the present invention, a plurality of indicators can be utilized that are responsive to different sterilization environments. For example, in one such embodiment different indicators responsive to different temperatures can be utilized such that the temperature to which the object to be sterilized can be indicated as within a range of temperatures.

There are a wide variety of suitable sterilizing agent sensitive substances for use. As an example for steam sterilization, a number of substance have sulfur-containing radicals that will decompose (for example, to metal sulfide) under steam sterilization conditions with a pronounced color change. Metal sulfides tend to be strongly colored and are often the most stable form of metal sulfur-containing substances. Furthermore, metal sulfides are often insoluble in water and may be held in a binder to prevent staining. The preferred sulfur-containing radical comprises thiosulfate, although other groups may be employed, for example polythionates, etc.

Substances for use as the primary color change component can include: lead thiosulfate, which is white in color and decomposes to yield black lead sulfide under steam sterilization conditions; copper thiosulfate, which is yellow in color and decomposes to yield black copper sulfide under steam sterilization conditions; ferrous thiosulfate, which is light green in color and decomposes to yield a black sulfide under steam sterilization conditions; nickel thiosulfate, which is light green in color and decomposes to black/green nickel sulfide under steam sterilization conditions; cobalt thiosulfate which is light red/purple in color and decomposes to deep purple/black cobalt sulfide under steam sterilization conditions; bismuth thiosulfate, which is orange/brown in color and decomposes to black bismuth sulfide under steam sterilization conditions; chromium thiosulfate, which is gray/blue in color and decomposes to dark green chromium sulfide under steam sterilization conditions; and/or silver thiosulfate, which is brown in color and decomposes to black silver sulfide under steam sterilization conditions.

Precursors of such sulfur-containing substances may be used that will yield the sulfur-containing substances under aqueous conditions. For example, lead carbonate and sodium thiosulfate may be employed as the color change component in the ink. These substances undergo a double decomposition reaction to yield lead thiosulfate under aqueous conditions. During the steam sterilization cycle, lead thiosulfate is initially formed which then decomposes to lead sulfide providing the desired color change.

In the case of an ethylene oxide sterilization process, ethylene oxide is sometimes diluted with a gas inert to the ethylene oxide, such as Freon, a fluoro-chloro substituted ethane, or CO2. Freon is a registered trademark for several different chlorofluorocarbons or CFCs belonging to E.I. du Pont de Nemours & Company 1007 Market Street, Wilmington, Del. 19898. The Freon selected should be a gas at the sterilization temperature. The concentration of ethylene oxide could be about 450 mg/liter to about 1,500 mg/liter, while processing temperatures can range from about 70° F. to about 140° F. Preferably, where the diluent is Freon, the ethylene oxide concentration is about 12 wt. % in the sterilant gas. Where the diluent is $CO_2$, the concentration of ethylene oxide is about 10 wt. %. For such processes, the parameters which affect ethylene oxide sterilization processes are exposure time, ethylene oxide concentration, temperature and humidity. For diluted ethylene oxide, relative humidities below 30% RH limit the effectiveness of the ethylene oxide sterilization process. High humidity, for example, above 90% relative humidity, can also result in inadequate processing.

In the case of a liquid peracetic acid sterilizer, sterilizing agent sensitive substance preferably includes a halide salt that, when subjected to an oxygen source, is oxidized to release a free halide. The free halide halogenates a dye causing it to change from a first color to a second color. The preferred halide is a salt of an alkali or alkaline earth metal, for example, potassium bromide. A suitable dye is phenol red, preferably the sodium salt thereof.

Sterilizing agent sensitive substance for a peracetic acid sterilizer may comprise a colorant susceptible to halogenation. Such an indicating ink may comprise fluorescein and/or phenol red. Illustrative nonlimiting examples of alkaline earth halide salts useful for a sterilizing agent sensitive substance for peracetic acid procedures include magnesium bromide, magnesium chloride, and potassium bromide. Each salt should be associated with a dye that can be halogenated by free halogen liberated by the reaction of halide with the peracetic acid. The resulting halogenated dye should have a color that is distinguishable from the dye selected as the starting material to be halogenated. Dyes having those required characteristics can be readily selected based on their chemical properties.

Illustrative non-limiting examples of dyes suitable for use in a sterilizing agent sensitive substance are phenol red, fluorescein, ethyl red, thymol blue, Acid Fuchsin, m-cresol purple, bromophenol blue, bromocresol green, and cresol red. Each dye can be used in combination with magnesium bromide applied to a backing and exposed to hydrogen peroxide vapor, which results in the following color changes indicated in following chart:

| Dye | Initial Color | Color Change |
|---|---|---|
| Ethyl Red | Light Pink | Light Yellow |
| Thymol Blue | Yellow-Orange | Light Yellow |
| Bromothymol Blue | Yellow | Yellow |
| m-Cresol Purple | Faded Yellow | Sky Blue |
| Bromophenol Blue | Yellow | Light Blue |
| Bromocresol Purple | Yellow | Faded Yellow |
| Bromocresol Green | Yellow | Yellow-Green |
| Cresol Red | Light Yellow | Lighter Yellow |

A sterilizing agent sensitive substance may be formulated to be any of the classes of chemical indicators found in Sterilization of Health Care Products-Chemical Indicators-Part 1: General Requirements, ANSI/AAMI ST 60-(1996) (a copy of which is attached as an Appendix, which is incorporated by reference). For example, the sterilizing agent sensitive substance may comprise a process indicator for steam sterilization and the components of the sterilizing agent sensitive substance may be selected so that the sterilizing agent sensitive substance satisfies the 121° Celsius test defined in Section 6.1 of the Sterilization of Health Care Products-Chemical Indicators-Part 1: General Requirements, ANSI/AAMI ST 60-(1996) (referencing the test methods described in ANSI/AAMI ST 45-1992, Bier/Steam vessels, a copy of which is attached as an Appendix, which test methods are herein incorporated by reference) in that:
a) after exposure to a previously stabilized condition of dry heat at 140° Celsius (plus or minus two degrees Celsius) for 30 minutes (plus or minus one minute), the sterilizing agent sensitive substance shows either no change or a change that is markedly-different from the change occurring after exposure to the steam sterilization process; and
b) the second indication (e.g. the second color) shall not occur until the sterilization indicator has been exposed to saturated steam for not less than 2 minutes at 121° Celsius (+3/−0 degrees Celsius); and
c) the second indication shall occur after the sterilization indicator is subjected to saturated steam for not more than 10 minutes at 121° Celsius is (+3/−0 degrees Celsius).

The components of the sterilizing agent sensitive substance also may be selected so that the sterilizing agent sensitive substance satisfies the 134° Celsius test defined in Section 6.1 of the Sterilization of Health Care Products-Chemical Indicators-Part 1: General Requirements, ANSI/AAMI ST 60-(1996) (again referencing the test methods described in ANSI/AAMI ST 45-1992, Bier/Steam vessels) in that:
a) after exposure to a previously stabilized condition of dry heat at 140° Celsius (plus or minus two degrees Celsius) for 30 minutes (plus or minus one minute), the sterilization indicator shows either no change or a change that is markedly different from the change occurring after exposure to the steam sterilization process; and
b) the second indication shall not occur until the sterilization indicator has been exposed to saturated steam for not less than 20 seconds at 134° (+3/−0 degrees Celsius); and
c) the second indication shall occur after the sterilization indicator is subjected to saturated steam for not more than 2 minutes at 134° Celsius (+3/−0 degrees Celsius).

Optionally, for purposes of steam sterilization the components of the sterilizing agent sensitive substance may be selected so that it satisfies both the 121° Celsius test and the 134° Celsius test defined in Section 6.1 of the Sterilization of Health Care Products-Chemical Indicators-Part 1: General Requirements, ANSI/AAMI ST 60-(1996). In the case of a sterilizing agent sensitive substance for an ethylene oxide sterilization process, the ANSI/AAMI guidelines include tests for ethylene oxide sterilization processes. Sterilization of Health Care Products-Chemical Indicators-Part 1: General Requirements, ANSI/AAMI ST 60-(1996) references test methods described in ANSI/AAMI ST 44-1992 BIER/EO gas vessels (a copy of which is attached as an Appendix, which test methods are herein incorporated by reference). The sterilizing agent sensitive substance could be formulated to meet the guidelines for ethylene oxide sterilization processes as well.

The sterilizing agent sensitive substance may optionally comprise an integrating indicator. That is, the sterilizing agent sensitive substance is formulated so that it reacts to all critical parameters over a specific range of a predetermined sterilization process. For a steam sterilization process, for example, the critical parameters are time, temperature and saturated steam.

While the invention has been described with specific embodiments, other alternatives, modifications and variations will be apparent to those skilled in the art. Accordingly, it will be intended to include all such alternatives, modifications and variations set forth within the spirit and scope of the appended claims.

What is claimed is:

1. A packaging system for a sterilizable article comprising: a sterilization pouch comprising a uniform material; and an integral sterilization indicator that repeats as a pattern throughout the interior surface of the sterilization pouch, wherein when the sterilization pouch is in a first position, the pattern on the interior surface of the sterilization pouch is not visible, and when the sterilization pouch is in a second position, the pattern on the interior surface of the sterilization pouch is visible, and wherein the integral sterilization indicator comprises a plurality of chemical indicators that are responsive to different sterilization environments.

2. The packaging system of claim 1 further wherein the sterilization pouch includes a posterior portion attached to an anterior portion along three edges, wherein the posterior and anterior portions define the sterilization pouch.

3. The packaging system of claim 1 further wherein the sterilization pouch comprising a sterilizable, flexible, elongate-tubular member having an outside, a closed end and an open end.

4. The packaging system of claim 1 further wherein a top part of the sterilization pouch is inverted so that the inside part of the sterilization pouch is facing outward and forms a cuff around the sterilization pouch.

5. The packaging system of claim 4 further wherein the integral sterilization indicator is located on the interior of the sterilization pouch below the cuff.

6. The packaging system of claim 5 further wherein the integral sterilization indicator is located on the interior of the sterilization pouch immediately below the cuff.

7. The packaging system of claim 4 further wherein the integral sterilization indicator is located on the cuff.

8. The packaging system of claim 1 further wherein the integral sterilization indicator is located on the exterior of the sterilization pouch.

9. The packaging system of claim 1 further wherein the integral sterilization indicator comprises a sterilizing agent sensitive substance.

10. The packaging system of claim 9 further wherein the sterilizing agent sensitive substance comprises a first indicating state prior to exposure to a sterilization procedure and a second indicating state after exposure to the sterilization procedure.

11. The packaging system of claim 10 further wherein the first indicating state comprises a first color and the second indicating state comprises a color that is visually distinguishable from the first color.

12. The packaging system of claim 9 further wherein the sterilizing agent sensitive substance comprises a first color prior to exposure to a sterilization procedure and comprises a second color that is visually distinguishable from the first color after exposure to the sterilization procedure.

13. The packaging system of claim 12 further wherein the first color comprises a substantially clear or transparent or translucent state, and the second color comprises a substantially opaque or colored state.

14. The packaging system of claim 1 further wherein the integral sterilization indicator comprises an indicator ink printed on the interior of the pouch.

15. The packaging system of claim 9 further wherein the sterilizing agent sensitive substance is responsive to hydrogen peroxide sterilization.

16. The packaging system of claim 9 further wherein the sterilizing agent sensitive substance is responsive to steam sterilization.

17. The packaging system of claim 16 further wherein the sterilizing agent sensitive substance includes sulfur-containing radicals that decompose under steam sterilization conditions to become a visually distinct.

18. The packaging system of claim 16 further wherein the sterilizing agent sensitive substance includes sulfur-containing radicals that decompose under steam sterilization conditions with a pronounced color change.

19. The packaging system of claim 17 further wherein the sterilizing agent sensitive substance includes sulfur-containing radicals that decompose to metal sulfide under steam sterilization conditions.

20. The packaging system of claim 9 further wherein the sterilizing agent sensitive substance is responsive to ethylene oxide sterilization.

21. The packaging system of claim 20 further wherein the sterilizing agent sensitive substance comprises 4(4-nitrobenzyl)pyridine.

22. The packaging system of claim 9 further wherein the sterilizing agent sensitive substance is responsive to peracetic acid sterilization.

23. The packaging system of claim 22 further wherein the sterilizing agent sensitive substance comprises a colorant susceptible to halogenation.

24. The packaging system of claim 23 further wherein the colorant comprises an indicating ink.

25. The packaging system of claim 24 further wherein the indicating ink may comprises fluorescein or phenol red or both.

26. The packaging system of claim 9 further wherein the sterilizing agent sensitive substance comprises a dye selected from the group of dyes suitable for use in a sterilizing agent sensitive substance and combinations thereof.

27. The packaging system of claim 26 further wherein the dyes are selected from the group comprising phenol red, fluorescein, ethyl red, thymol blue, Acid Fuchsin, m-cresol purple, bromophenol blue, bromocresol green, cresol red, and combinations thereof.

28. The packaging system of claim 9 further wherein the sterilizing agent sensitive substance is formulated to be of the classes of chemical indicators found in Sterilization of Health Care Products-Chemical Indicators-Part 1: General Requirements, ANSI/AAMI ST 60-(1996).

29. The packaging system of claim 9 further wherein the sterilizing agent sensitive substance satisfies the 121° Celsius test defined in Section 6.1 of the Sterilization of Health Care Products-Chemical Indicators-Part 1: General requirements, ANSI/AAMI ST 60-(1996).

30. The packaging system of claim 9 further wherein the sterilizing agent sensitive substance satisfies the 134° Celsius test defined in Section 6.1 of the Sterilization of Health Care Products-Chemical Indicators-Part 1: General Requirements, ANSI/AAMI ST 60-(1996).

31. The packaging system of claim 9 further wherein the sterilizing agent sensitive substance satisfies both the 121° Celsius test and the 134° Celsius test defined in Section 61 of the Sterilization of Health Care Products-Chemical Indicators-Part 1: General Requirements, ANSI/AAMI ST 60-(1996).

32. The packaging system of claim 9 further wherein the sterilizing agent sensitive substance satisfies the tests for ethylene oxide sterilization processes defined in Sterilization of Health Care Products-Chemical Indicators-Part 1: General Requirements, ANSI/AAMI ST 60-(1996).

33. The packaging system of claim 1 further wherein the sterilizing agent sensitive substance is formulated so that it reacts to critical parameters over a specific range of a sterilization process.

34. The packaging system of claim 33 further wherein the sterilizing agent sensitive substance reacts to the parameters of a steam sterilization process.

35. The packaging system of claim 34 further wherein the sterilizing agent sensitive substance reacts to the parameters of time, temperature and saturated steam.

36. A packaging system for a sterilizable article comprising:
   a sterilization pouch comprising a uniform material;
   a top part of the sterilization pouch inverted so that the inside part of the sterilization pouch is facing outward and forms a cuff around the sterilization pouch; and
   an integral sterilization indicator that repeats as a pattern throughout the interior surface of the sterilization pouch below the cuff, wherein when the sterilization pouch is in a closed position, the pattern on the interior surface of the sterilization pouch is not visible, and when the sterilization pouch is in an open position, the pattern on the interior surface of the sterilization pouch is visible,
   wherein the integral sterilization indicator comprises a plurality of chemical indicators that are responsive to different sterilization environments.

37. The packaging system of claim 36 further wherein the integral sterilization indicator is located on the interior of the sterilization pouch below the cuff.

38. The packaging system of claim 37 further wherein the integral sterilization indicator is located on the interior of the sterilization pouch immediately below the cuff.

39. The packaging system of claim 36 further wherein the integral sterilization indicator is located on the cuff.

40. The packaging system of claim 36 further wherein the integral sterilization indicator comprises a sterilizing agent sensitive substance.

41. The packaging system of claim 40 further wherein the sterilizing agent sensitive substance comprises a first indicating state prior to exposure to a sterilization procedure and a second indicating state after exposure the sterilization procedure.

42. The packaging system of claim 40 further wherein the sterilizing agent sensitive substance comprises a dye selected from the group of dyes suitable for use in a sterilizing agent sensitive substance and combinations thereof.

43. A packaging system for a sterilizable article comprising:
   a sterilization pouch comprising a uniform material, and adapted to aseptically deliver a sterilized article by inverting the pouch; and
   an integral internal sterilization indicator that repeats as a pattern throughout the interior surface of the sterilization pouch, wherein when the sterilization pouch is in a closed position, the pattern on the interior surface of the sterilization pouch is not visible, and when the sterilization pouch is inverted during aseptic delivery of the sterilized article, the pattern on the interior surface of the sterilization pouch becomes visible,
   wherein the integral sterilization indicator comprises a plurality of chemical indicators that are responsive to different sterilization environments.

44. The packaging system of claim 43 further wherein a top part of the sterilization pouch is inverted so that the inside part of the sterilization pouch is facing outward and forms a cuff around the sterilization pouch.

45. The packaging system of claim 44 further wherein the integral internal sterilization indicator is located on the interior of the sterilization pouch below the cuff.

46. The packaging system of claim 45 further wherein the integral internal sterilization indicator is located on the cuff.

47. The packaging system of claim 43 further wherein the integral internal sterilization indicator comprises a sterilizing agent sensitive substance.

48. The packaging system of claim 47 further wherein the sterilizing agent sensitive substance comprises a first indicating state prior to exposure to a sterilization procedure and a second indicating state after exposure to the sterilization procedure.

49. The packaging system of claim 47 further wherein the integral internal sterilization indicator comprises an indicator ink printed on the interior of the pouch.

50. The packaging system of claim 47 further wherein the integral internal sterilization indicator comprises an indicator ink printed on the exterior of the pouch.

51. The packaging system of claim 40 further wherein the sterilizing agent sensitive substance is responsive to hydrogen peroxide sterilization.

52. The packaging system of claim 40 further wherein the sterilizing agent sensitive substance is responsive to steam sterilization.

53. The packaging system of claim 40 further wherein the sterilizing agent sensitive substance is responsive to ethylene oxide sterilization.

54. The packaging system of claim 40 further wherein the sterilizing agent sensitive substance is responsive to peracetic acid sterilization.

55. The packaging system of claim 47 further wherein the sterilizing agent sensitive substance comprises a dye selected from the group of dyes suitable for use in a sterilizing agent sensitive substance and combinations thereof.

\* \* \* \* \*